(12) United States Patent
Honeck

(10) Patent No.: US 7,512,446 B2
(45) Date of Patent: Mar. 31, 2009

(54) LEAD FIXATION TOOL

(75) Inventor: Jordon D. Honeck, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 488 days.

(21) Appl. No.: 10/693,272

(22) Filed: Oct. 24, 2003

(65) Prior Publication Data

US 2005/0090884 A1 Apr. 28, 2005

(51) Int. Cl.
*A61N 1/00* (2006.01)
*A61B 19/00* (2006.01)
*B23Q 3/12* (2006.01)

(52) U.S. Cl. .................. 607/116; 279/43.5; 606/129
(58) Field of Classification Search ............... 607/1–2, 607/116–131; 279/62, 42–43.8; 606/129
See application file for complete search history.

(56) References Cited

U.S. PATENT DOCUMENTS

| | | | | |
|---|---|---|---|---|
| 3,110,093 A | * | 11/1963 | Johnson | 29/747 |
| 3,565,078 A | * | 2/1971 | Vailliancourt et al. | 604/256 |
| 5,137,288 A | * | 8/1992 | Starkey et al. | 279/42 |
| 5,152,298 A | * | 10/1992 | Kreyenhagen et al. | 607/116 |
| 5,330,204 A | * | 7/1994 | Huff et al. | 279/62 |
| 5,971,958 A | * | 10/1999 | Zhang | 604/165.02 |
| 6,033,414 A | * | 3/2000 | Tockman et al. | 606/129 |
| 6,120,480 A | * | 9/2000 | Zhang et al. | 604/164.01 |

* cited by examiner

*Primary Examiner*—Mark W Bockelman
(74) *Attorney, Agent, or Firm*—Stephen W. Bauer; Daniel G. Chapik

(57) ABSTRACT

A lead fixation tool includes a tapered opening for receiving and guiding a stylet into a lead. The fixation tool also includes an engagement mechanism for gripping a portion of the lead connector so that rotation of the tool causes rotation of an active fixation tip, such as a helical tip, coupled with the lead.

26 Claims, 4 Drawing Sheets

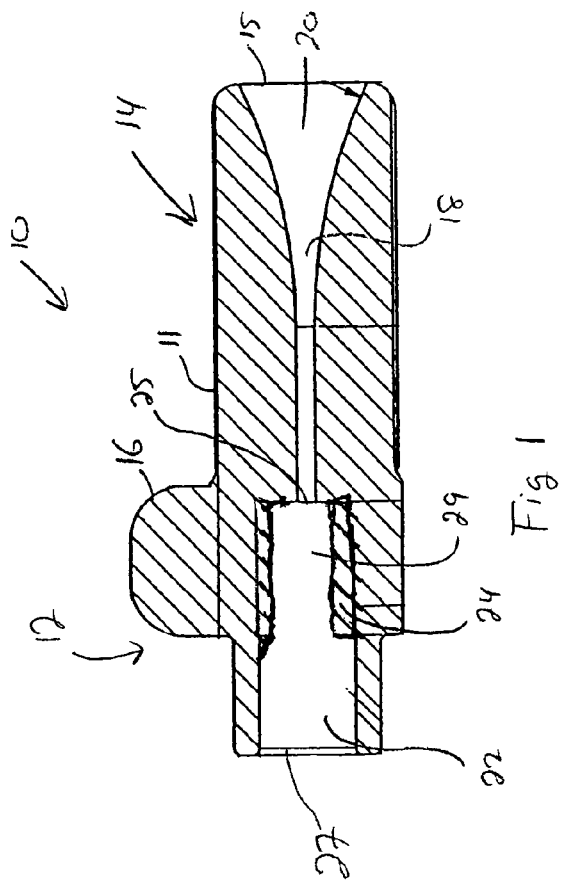
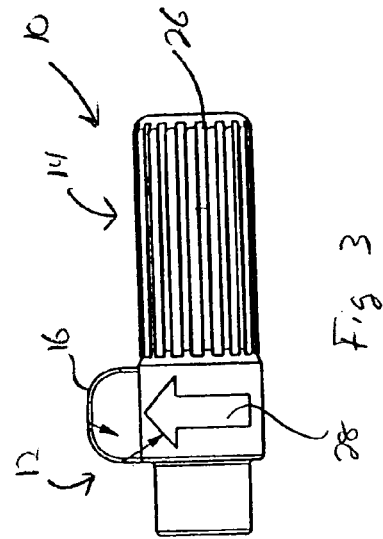
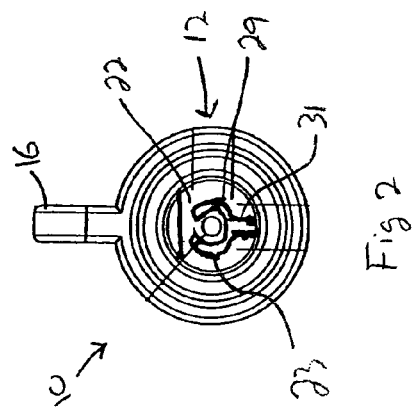
Fig. 1
Fig. 3
Fig. 2

LEAD FIXATION TOOL

BACKGROUND OF THE INVENTION

1. Field of the Invention

The present invention generally relates to implantable medical devices. More specifically, the present invention relates to leads for implantable medical devices.

2. Description of the Related Art

Various implantable medical devices (IMD) utilize leads to deliver electrical stimulation to tissue, receive sensed electrical impulses from tissue, or transfer other sensor data indicative of a physical parameter. For example, implantable cardiac pacemakers, cardioverters, or defibrillators commonly have one or more leads connecting the device to cardiac tissue. The leads are often passed through a vein and guided into an atrial or ventricular chamber of the heart. Once so located, the distal end of the lead is properly positioned and often is secured.

Various techniques are employed to secure the distal end of the lead within the heart. For example, some lead tips include tines that engage fibrous tissue along the interior wall of the cardiac chamber. Over time, additional fibrous growth occurs that further secures the lead in position. Other leads include active fixation such as, for example, a helical tip that can be rotated into the cardiac tissue. Such a helical tip can serve as a fixation means, but may also serve as an electrode that is electrically coupled with one or more electrical conductors passing through the lead body. In use, the distal end of the lead is positioned in the selected location. The proximal end of the lead, or a portion thereof, is rotated which causes the helical tip to rotate and advance into the tissue. In order to facilitate this rotation, a clamping tool or wrench is coupled with the distal portion of the lead. Typically, the tool engages a connector pin and provides a larger gripping surface for the implanting physician to rotate. One such device is structured to engage the connector pin and provide an elongated pair of handles (scissor configuration) that extend perpendicular to a central axis of the connector pin. The implanting physician then grips a portion of the lead body distal to the connector pin and the rotates the tool in a plane perpendicular to the central axis until the helical tip is secured. Generally, such a wrench is relatively large and encumbers a large portion of the surgical field. Thus, wrench is typically only attached just prior to active fixation of the lead and is then removed. Furthermore, the "wrapping" action required to use the wrench may be cumbersome.

In addition, many leads are provided with a lumen disposed through the entirety of the lead body. The lumen may receive a guidewire that has been previously positioned, thereby allowing the lead to be directed to the proper location by passing over the guidewire. In such a case, the proximal end of the guidewire is inserted into the distal end of the lumen in the lead. Conversely, a stylet may be inserted into the lumen to provide a degree of rigidity to promote steerability of the lead in order to facilitate its passage into the proper position.

When a stylet is used, the distal end of the stylet is inserted into the proximal opening of the lumen in the lead and then advanced. To facilitate this insertion, a funnel is temporarily coupled with the connector. The funnel provides an enlarged opening and a guide through which the distal end of the stylet is inserted. The funnel guides the stylet into the narrower opening of the lumen in the connector pin. Once the stylet is inserted, the funnel generally remains in place. Thus, there is balance between providing a large opening to facilitate insertion while providing a small enough structure so as to minimize hindrance during the lead manipulation as well as fixation of the tip.

BRIEF SUMMARY OF THE INVENTION

The present invention, in one embodiment, includes a fixation tool that engages a proximal portion of a lead allowing torque to be applied that causes a lead tip to engage cardiac tissue. The fixation tool further includes a guide passage disposed through the tool that aligns with the lumen of the lead to facilitate insertion of a stylet through the passage and into the lumen In one embodiment, the fixation tool includes a proximal portion and a distal portion that are rotatably coupled to one another. The guide passage disposed within the proximal portion has a tapered shape that narrows in the direction of the distal end. The distal portion includes a handle structure that provides a gripping position.

In one embodiment, a tracking mechanism is coupled with the proximal portion, engages the distal portion, and provides an indication when a the proximal portion has passed through a complete revolution relative to the distal portion. The tracking mechanism, in one embodiment is a biased member that engages a structure disposed on the distal portion to provide an audible or tactile indication. The tracking mechanism may include a ball or pin that engages a detent disposed on a portion of the distal portion.

In one embodiment, the present invention is a lead fixation tool comprising a proximal portion having a tapered passage therethrough. The tool also includes a distal portion having a channel that is axially aligned with the passage and having a lead pin engagement mechanism.

In another embodiment, the present invention is a lead fixation tool comprising means for engaging a lead and means for aligning the lead with a passageway. In another embodiment, the present invention is a tool comprising means for receiving a stylet. The tool also includes means for receiving a lead aligned with the means for receiving the stylet and means for gripping the lead.

In another embodiment, the present invention is a lead fixation tool comprising a proximal portion having a guide passage disposed therethrough, wherein the guide passage includes a tapered portion having an opening and a lumen interface. The tool also includes a distal portion having a connector channel that is axially aligned with the guide passage and an engagement collar disposed within the connector channel that is configured for gripping and axially aligned with the guide passage.

In another embodiment, the present invention is a lead fixation tool comprising a housing having a generally circular cross section, the housing including a proximal portion and a distal portion, wherein the proximal portion and the distal portion are axially aligned. The tool also includes a guide passage extending between an opening in the proximal portion to a lumen interface, wherein the guide passage tapers from the opening to a narrow diameter for receiving stylet and a lead receiving channel disposed within the distal end for receiving at least a portion of a connector assembly of a lead. The tool also includes a connector pin channel disposed within the lead receiving channel for receiving a connector pin of the connector assembly and axially aligning the connector pin with the lumen interface and an engagement collar defining the connector pin channel and configured to grip the connector pin.

The present invention also includes a method of manipulating a lead comprising inserting a lead connector of a lead having a lumen opening into a distal portion of a fixation tool that grips the lead connector and aligns the lumen opening with a guide passage disposed within a proximal portion of the fixation tool. The method also includes inserting a stylet through the proximal portion of the fixation tool and into the lumen opening and rotating the fixation tool to cause rotation of an active fixation lead tip coupled with the lead.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is a side sectional view of a fixation tool consistent with the principles of present invention.

FIG. 2 is a front, planar view of the fixation tool of FIG. 1.

FIG. 3 is side elevational view of the fixation tool of FIG. 1.

DETAILED DESCRIPTION

Figure 4:
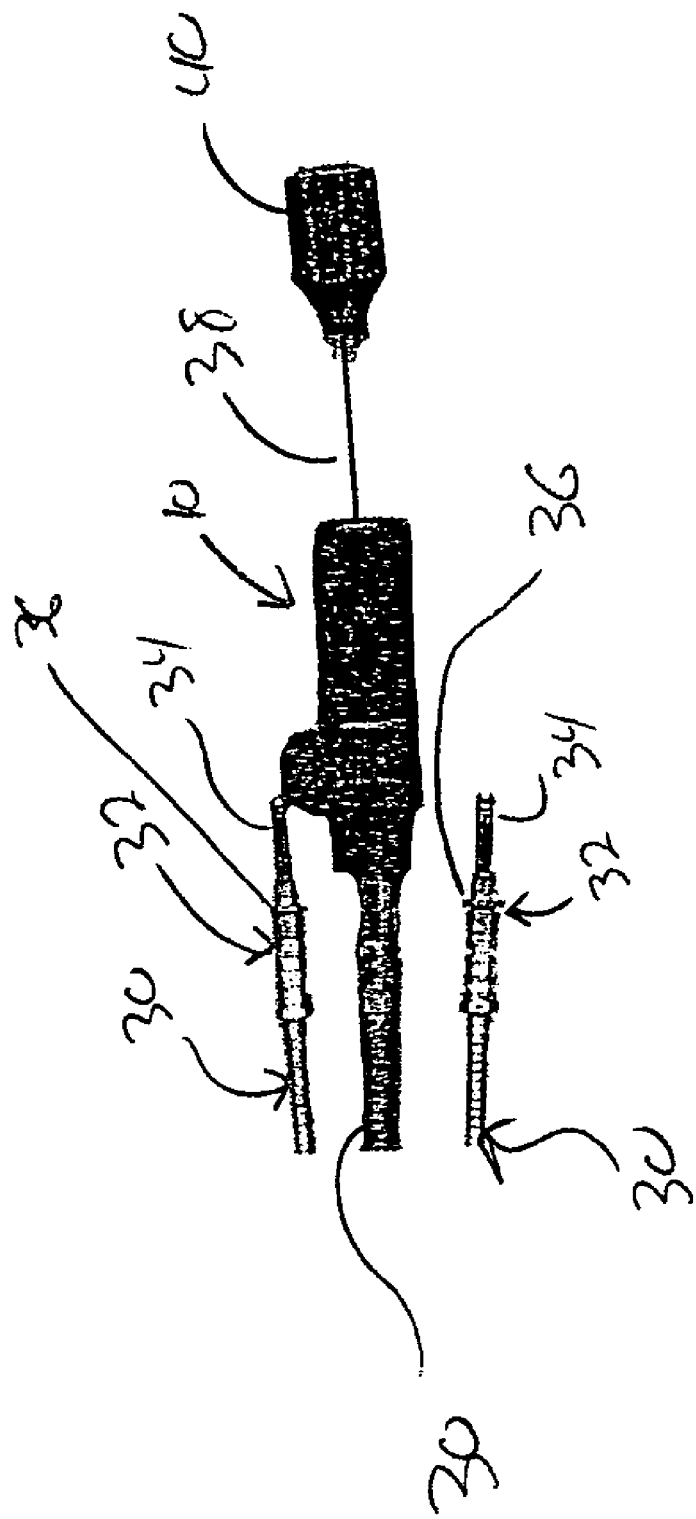
FIG. 4 is planar view of the fixation tool coupled with a lead, proximate two additional leads, with a stylet inserted through the fixation tool.

FIG. 1 is a side sectional view of a fixation tool 10. The fixation tool 10 includes a distal portion 12 and proximal portion 14 that to form a housing 11. As illustrated, the proximal portion 10 and the distal portion 12 are integral and provide a rigid tool 10. In other embodiments discussed below, the proximal portion 10 and the distal portion 12 are rotatably coupled together.

The fixation tool 10 can be fabricated from any suitable material, including plastic or metal, that can be properly sterilized for use in a surgical field. In one embodiment, the fixation tool 10 is an integral unit that is molded from plastic. In other embodiments, separate components are coupled together to form the fixation tool 10.

As illustrated in FIGS. 1 and 2, the fixation tool 10 includes a handle 16 disposed on the distal portion 12. The handle 16 is a relatively narrow tab that extends outward from the distal portion 12. The handle 16 can be used as a gripping surface to engage the tool 10. Alternatively, the distal portion 12 may be provided with a gripping or textured surface (e.g., ridges) to facilitate gripping if the handle 16 is not provided, though neither the handle or the textured surface is required.

The handle 16 provides a visual position marker. That is, the tool 10 is rotated during use. By monitoring the relative position of the handle 16, the implanting physician can determine how far the tool 10 has been rotated and can count complete revolutions. Thus, during affixation of a lead, the implanting physician rotates the tool 10 a predetermined number of times to assure securement. By noting the initial position of the handle 10 and then monitoring the movement of the handle 16 (visually or by touch), the implanting physician is able to know the effective rotation imparted to a tip of the lead. The handle 16 provides one mechanism for monitoring rotations of the tool 10.

As illustrated, one handle 16 is provided. Additional handles, one or more handles of different shapes, or alternative gripping portions could be provided. In addition, no handle could be provided and a visual or other marker could be disposed on the distal portion 12 as a rotational marker.

A guide passage 18 is disposed within the proximal portion 14. A funnel or tapered portion 20 of the guide passage 18 provides an exposed opening 15 into the guide passage 18. The size of the opening 15 is selected to be larger than the diameter of a stylet or other implement that is inserted therein. In one embodiment, the opening 15 is made as large as possible relative to the diameter of the proximal portion 14, while maintaining structural integrity, in order to facilitate easy location and insertion of the stylet. An interior surface defined by the tapered portion 20 is relatively smooth so that a tip of the stylet or other implement can slide over the surface. The tapered portion 20 narrows or tapers in diameter until a minimal diameter is reached. The minimal diameter is selected to accommodate and accurately direct the appropriate stylet, guidewire, or other implement passed through the tool 10. The guide passage opens with the distal portion 12 and effectively terminates at a lumen interface 25.

A lead receiving channel 22 is disposed within the distal portion 12 and includes a lead receiving opening 27. The lead receiving channel 22 has a diameter that allows a proximal portion of a lead to be inserted and guides the lead towards the lumen interface 25. A connector pin channel 29 is disposed between the lead receiving channel 22 and the lumen interface 25. Functionally, the connector pin channel 29 serves to accurately position the lead so that a lead lumen is aligned with the guide passage 18. In addition, the connector pin channel 29 acts to grip the connector pin so that torque can be applied to the connector pin by rotating the fixation tool 10. Alternatively, the lead receiving channel alone, or in combination with the connector pin channel 29 is configured to grip the lead. As used herein, the term grip is meant to include any mechanism by which the lead is reverseably coupled with the tool 10 so that rotation of tool 10 causes rotation of at least the gripped portion of the lead. Gripping includes but is not limited to clamping, squeezing, locking, sliding, compressing, screwing, twisting, snapping, interlocking, or otherwise causing appropriate engagement between the tool 10 and the lead.

In one embodiment, the connector pin channel 29 is a chamber having a circular cross section defined by a connector engagement collar 24 and has a diameter selected such that the connector pin is forcibly insert able, thereby creating a frictional fit or lock. In such an embodiment, the material could be selected for the connector pin channel 29 that has some degree or resiliency to further facilitate the frictional fit. The connector engagement collar 24 could be an integral component of the tool 10 of a separate component. In another embodiment, the connector pin channel 29 is tapered and narrows in proximity to the lumen interface 25. Once again, the lead would be forcibly inserted and the tapered connector pin channel 29 would frictionally engage the lead. Alternatively, cross sectional shapes other than circular could be employed to facilitate the securement of the lead.

In the embodiment illustrated in FIG. 2, the connector engagement collar 24 is a resilient member having a C-shaped clamp 23 affixed to a base 31 and medially disposed within the lead receiving channel 22. The clamp 23 is resilient or spring biased so that insertion of the lead connector pin causes the clamp 23 to expand and generate an interference fit. Alternatively, other shapes, prong or clamp configurations could be employed.

In other alternative embodiments, the connector pin channel 29 and/or the lead receiving channel 22 are provided with active clamping mechanisms. That is, moveable portions (e.g., jaws) are provided that can be externally actuated to grip the connector pin when it is inserted into the tool 10. Such active clamping mechanisms could include a threaded or sliding assembly in cooperation with a collet, a threaded member positioned to selectively abut the connector pin, a lever assembly, or any number of known clamping mechanisms.

The particular mechanism selected to engage the lead connector pin will work in cooperation with the lead receiving channel 22 and the connector pin channel 29 (which may be defined by that mechanism) to align the lead lumen with the guide passage 18 and provide sufficient engagement with the lead so that torque can be applied. The C-shaped clamp 23 or equivalent interference fit arrangements provide for both and do not require additional actions to be taken by the implanting physician beyond insertion of the lead into the tool 10. The alternative active clamping mechanisms may be able to provide additional gripping force, but do require additional steps in their use along with additional components. Thus, the particular configuration selected will depend upon the leads being utilized and the active fixation requirements of those leads.

FIG. 3 is a side elevational view of the fixation tool 10 of FIGS. 1 and 2. As illustrated, a rotational indicator 28 is provided that illustrates the proper rotational direction for lead implantation. Such indicia is optional and may printed, stamped, painted, adhered or otherwise applied to the tool 10. Alternatively or in combination with the above, such indicia 28 may be formed by creating a raised or recessed marking on the tool 10.

The proximal portion 14 is provided with a griping surface to facilitate handling and rotation of the tool 10. In the embodiment illustrated, the gripping surface includes a plurality of ridges 26. Other surfaces and textures could be utilized.

Figure 5:
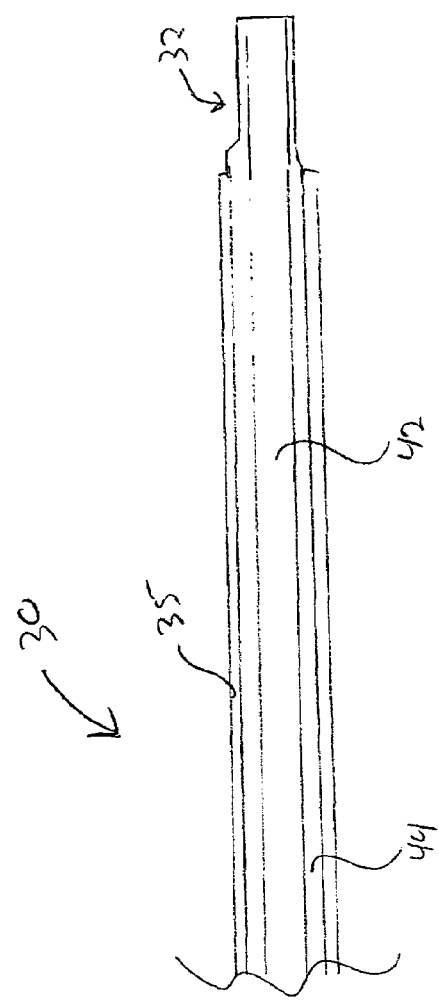
FIG. 5 is a stylized, partially sectional view of a lead having a helical fixation tip.
Figure 5:
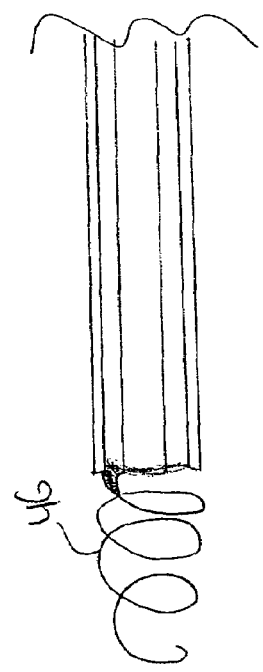

Referring to FIGS. 4 and 5, a number of leads 30 are illustrated, with the fixation tool 10 coupled with one lead 30. It should be appreciated that there are a variety of lead types, configurations and styles in use that have active fixation tips. Thus, the description provided of the leads 30 is meant to be exemplary and non-limiting in nature. Certain portions of the fixation tool 10 can be configured or adapted to cooperate with specific lead configurations.

In general, the lead 30 typically includes a lead body or sheath 35. Disposed within the sheath are one or more conductors 44 that electrically couple one or more electrodes (not separately shown) with a connector assembly 32. Each independent electrode will usually have an electrically isolated contact within the connector assembly 32. An active fixation mechanism is provided at the distal end of the lead 30. In the embodiment illustrated, the active fixation mechanism is a helical tip 46. Helical tip 46 may act as an electrode or may simply serve as a fixation means. In either case, the helical tip 46 is mechanically coupled to some portion of the connector assembly 32. Thus, rotation of the connector assembly 32 (or a portion thereof) causes the helical tip 46 to rotate. The mechanical coupling may be the conductor 44, a separate coupling member (not shown), or a combination thereof. Such rotation is typically relative to the sheath 35; however, in some embodiments, the entire lead 30 could be rotated.

A lead lumen 42 is disposed within the lead 30 and the connector assembly 32. The lead lumen 42 accommodates a stylet 38 or other implements, such as a guidewire. Typically, the lead lumen 42 is medially disposed or at least medially disposed within the connector assembly. Insertion of the stylet 38 provides additional rigidity to the lead 30 for manipulation and control during implantation, positioning, and/or removal of the lead 30.

Referring to FIGS. 1 and 4, the connector assembly 32 is inserted into the lead receiving channel 22. The connector assembly 32 includes, at its proximal end, a connector pin 34. In this lead 30 configuration, rotation of the connector pin 34 relative to or in combination with the remainder of the connector assembly 32, causes rotation of the helical tip 46. As the connector assembly 32 is further inserted, the connector pin 34 enters the connector pin channel 29. This entry can be facilitated by, for example, tapered or rounded portions defining the connector engagement collar 24 or the clamp 23.

The force required to insert the connector pin 34 into the connector pin channel 29 will depend upon the mechanism employed to grip the connector pin 34. For example, the resilient clamp 23 will require sufficient force to overcome the spring tension or resiliency of the clamp 23. A connector pin channel 29 providing a frictional lock will require sufficient force to overcome the frictional forces. With an active external clamping mechanism, seating the connector pin 29 would require little applied force, as the gripping force is selectively applied after insertion.

The connector pin 34 is inserted into the connector pin channel 29 as far as permissible. The connector pin 34 may abut the lumen interface 25 and/or a shoulder 36 of the connector assembly 32 may abut the connector engagement collar 24. Once positioned, the lead lumen 42 is axially aligned with the guide passage 18. The connector assembly 32 is effectively gripped within the connector pin channel 29, as previously discussed. Thus, subsequent rotation of the tool 10 will impart rotation on the connector pin 34 and the helical tip 46.

Once the lead 30 is inserted into the fixation tool 10, the stylet 38 is implemented by inserting a distal end of the stylet 38 into the opening 15. The tapered portion 20 guides the distal end of the stylet 38 into the guide passage 18. As the guide passage 18 and the lead lumen 42 are axially aligned, continued insertion causes the stylet 38 to enter into the lead lumen 42. Once so started, the stylet 38 can be advanced as far as desired within the lead 30. The stylet 38 typically includes a handle portion 40. The handle portion 40 may include a neck that can be partially received within the tapered portion 20, when the stylet 38 is fully inserted. The lead 30 is then manipulated as desired for implantation, explantation, positioning, or the like. Of course, once the tool 10 is coupled with the lead 30, a guidewire could be passed through the lead lumen 42 and out through the opening 15 rather than using a stylet 38, depending upon the desired application.

To cause the helical tip 46 to advance into tissue, the tool 10 is rotated a predetermined number of times. As previously discussed, the number of rotations can be monitored based on the position of the handle 16 or any other visual or tactile marker. Conversely, for extraction, the tool 10 is rotated in the opposite direction. In either case, rotation of the tool 10 causes the connector pin 34, the connector assembly 32, or some portion thereof to rotate. This rotation is translated through the lead body and causes the helical tip 46 to rotate.

To impart rotation, any part of the tool 10 is gripped and manually rotated. Rotation occurs while a central axis of the tool 10 is axially aligned with or parallel to the connector assembly 32. Optionally, the implanting physician can grip a portion of the lead 35 (or non-rotating portion of the connector assembly 32 if present) with one hand and grip the tool 10 with the other. Rotation is then imparted by the tool 10 relative to, for example, the sheath 35. Gripping the tool 10 can be facilitated by using the handle 16 and/or by gripping the ridges 26.

It should be appreciated that the tool 10 may be used to insert the stylet 38, may be used to rotate the active fixation tip of the lead, or may be used to both insert the stylet 38 and rotate the active fixation tip of the lead. That is, fixation tool 10 provides several functions that may be used alone or in combination.

In many lead procedures, the fixation tool 10 will be coupled with the lead 30 as described. The stylet 38 will be inserted and the helical tip 46 will be properly positioned. Then, with the stylet 38 still inserted, the helical tip 46 is secured. This process is facilitated through the use of the fixation tool 10 in that the tool 10 provides a single device that allows for the insertion of the stylet 38 and provides a mechanism for rotating the helical tip 46 in a non-obtrusive manner. Because of the configuration of the fixation tool 10 and the engagement with the lead 30, the fixation tool 10 is unlikely to unintentionally disengage and fall or slip, both periods of use and non-use. In addition, all of the functionality required is incorporated into a single device. Thus, there is no need to switch, disengage, or move one tool in order to allow the use of another.

Figure 6:
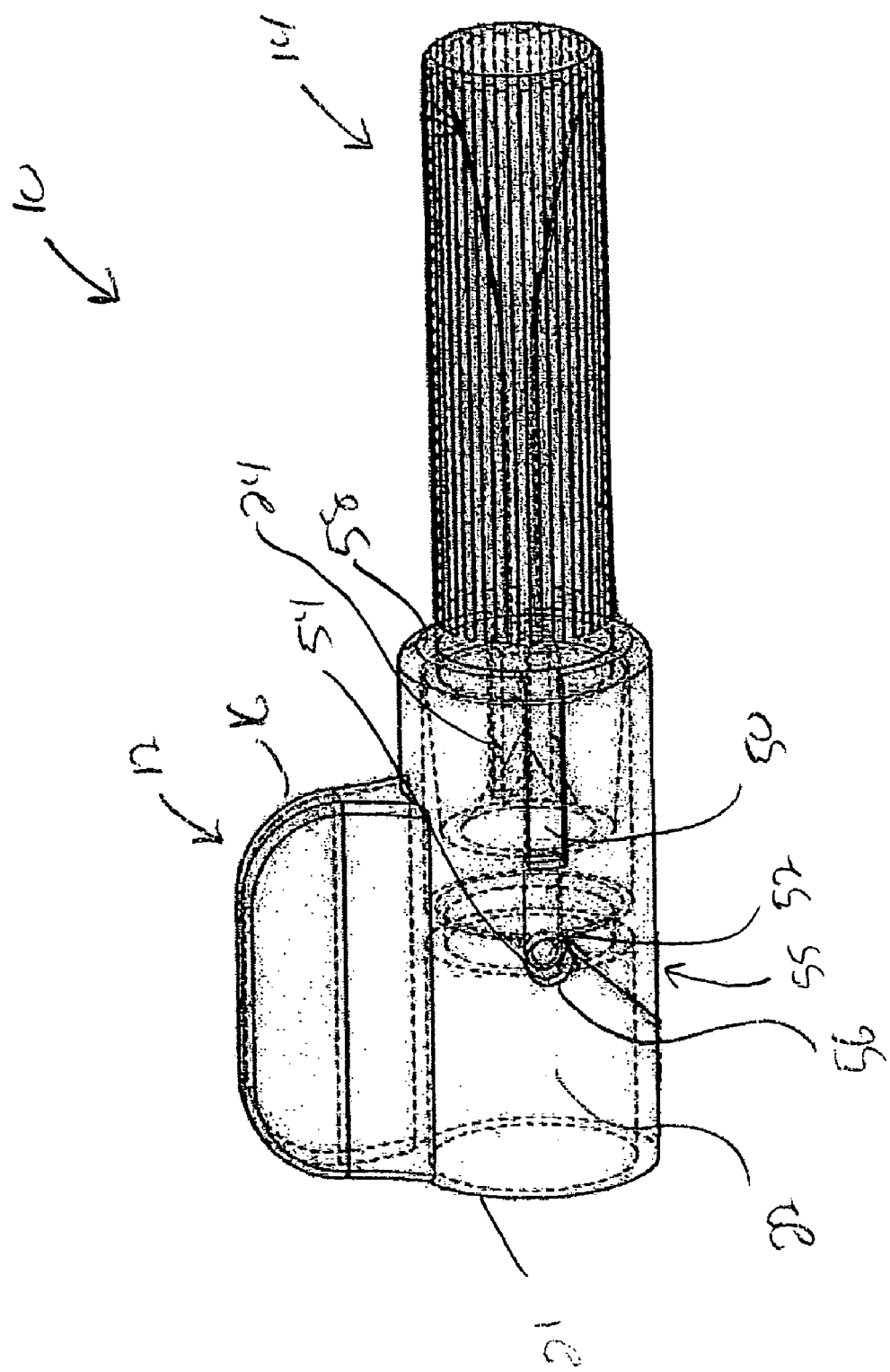
FIG. 6 is a partially sectional, side elevational view of a fixation tool having a proximal portion and a distal portion that are rotatable with respect to one another, consistent with the principles of the present invention.

FIG. 6 illustrates an alternative embodiment of the fixation tool 10. In this embodiment, the distal portion 12 and the proximal portion 14 are separate components that are rotatably coupled together. A bearing 58 is provided that couples the distal portion 12 and the proximal portion 14 while allowing relative rotation. In use, one portion is gripped and held while the other portion is gripped and rotated.

In order to aid in the counting of revolutions of the tool 10, a rotation indicator 55 is provided. Rotation indicator provides an audible and/or a tactile indication each time the distal portion 12 and the proximal portion travel through a complete rotation relative to one another. An arm 50 is coupled with the proximal portion 14 and extends into an interior portion of the distal portion 12. The arm 50 is biased outward. A ball 52 is attached to a terminal portion of the arm 50. A window 56 is provided in the distal portion 12. The window 56 is an opening in the distal portion 12 that is shaped to engage the ball 52. The window 56 may be an opening that extends through the entire thickness of a wall defining the distal portion 12. The window 56 may simply be an exposed opening or may be covered with a clear material such as plastic or glass. Alternatively, the window 56 extends only partially through the wall and is not visually perceivable external to the tool 10.

As the proximal portion 14 is rotated relative to the distal portion 12, the arm 50 and the ball 52 likewise rotate. Each time the ball 52 passes the window 56, outward bias of the arm 50 causes the ball to engage the window 56. This will produce an audible click; will provide a vibration or a snap that can be felt; and/or will be visually perceivable by observing the window. Various other mechanisms may be employed as a rotation counter. The components discussed may be located differently. For example, the arm 50 may depend from the distal portion 12 instead of the proximal portion. The ball 52 may be coupled with the distal portion 12 and engage a detent in the arm 50. Many other variations are contemplated as well. In addition, various electronic monitoring mechanisms could be employed as well. For example, for each revolution a tone could be produced or a light could be flashed. Alternatively, a resetable electronic counter could be employed to provide an indication of the number of revolutions.

As previously discussed, distal portion 12 rotates relative to proximal portion 14. Thus, the positioning and coupling of the connector engagement collar 24 determines which component effectuates rotation of the lead tip 46. For example, if the connector engagement collar 24 is fixedly coupled with the proximal portion 14, then rotation of the proximal portion 14 causes the helical tip 46 to rotate. Conversely, if the connector engagement collar 24 is fixedly coupled with the distal portion 12, then rotation of the distal portion 12 causes the helical tip 46 to rotate.

In the embodiment illustrated, the connector engagement collar 24 is fixedly coupled with the proximal portion 14. Thus, once the lead 30 is inserted, the implanting physician can grip the distal portion 12 and hold it steady with one hand. The proximal portion 14 is gripped in the other hand and then rotated to affix or extract the helical tip 46. The rotation indicator can be used to track the number of revolutions. Alternatively, a visual indicator can be provided on the proximal portion 14 to facilitate the monitoring of complete rotations. In this manner, the lead 30 can be affixed without holding any portion of the lead 30 outside of the tool 10.

One handed operation can be achieved by gripping the proximal portion 14 and rotating without gripping the distal portion 12. Though not illustrated, a locking mechanism can be provided to lock the distal portion 12 relative to the proximal portion 14. Thus, the fixation tool 10 would be utilized in much the same manner as described with reference to FIGS. 1-3

Although the present invention has been described with reference to preferred embodiments, persons skilled in the art will recognize that changes may be made in form and detail without departing from the spirit and scope of the invention.

The invention claimed is:

1. A lead fixation tool comprising:
a proximal portion having a tapered passage there through, with the tapered passage narrowing in a direction towards a distal portion; and
a distal portion having a channel in substantially axial alignment with the passage along a longitudinal axis, wherein the proximal portion and the distal portion are rotatably coupled so that relative rotation is permitted between the proximal portion and the distal portion; and
an expandable lead pin engagement mechanism disposed within the channel, wherein the engagement mechanism is a C-shaped interference clamp that is axially aligned with the passage and to grip a lead connector assembly and remain at a fixed location on said longitudinal axis during said relative rotation of said proximal and distal portions; and
a rotation indicator for indicating relative rotation between the proximal and distal portions the rotation indicator includes:
a resilient arm having an actuator; and
a detent, wherein rotation of the distal portion relative to the proximal portion causes the actuator to engage the detent and provide a signal.

2. The lead fixation tool of claim 1, wherein the proximal portion and the distal portion form an integral housing.

3. The lead fixation tool of claim 1, further comprising a bearing, wherein the bearing couples the distal portion and the proximal portion.

4. The lead fixation tool of claim 1, wherein the signal is audible.

5. The lead fixation tool of claim 1, wherein the signal is a tactile sensation.

6. The lead fixation tool of claim 1, further comprising a handle depending from the distal portion.

7. A lead fixation tool comprising:
a proximal portion having a guide passage disposed there through, wherein the guide passage includes a tapered portion having an opening and a lumen interface, with the tapered portion narrowing in a direction from the opening to the lumen interface; and
a distal portion having a connector channel that is axially aligned with the guide passage along a longitudinal axis, wherein the proximal portion and the distal portion are rotatably coupled so that relative rotation is permitted between the proximal portion and the distal portion;
an expandable engagement collar disposed within the connector channel that is configured for gripping and axially aligned with the guide passage, wherein the engagement collar is a C-shaped interference clamp that is axially aligned with the passage to grip a lead connector assembly and remain at a fixed location on said longitudinal axis during said relative rotation of said proximal and distal end portions; and
a rotation indicator for indicating relative rotation between the proximal and distal portions wherein the rotation indicator includes:
a resilient arm having an actuator; and
a detent, wherein rotation of the distal portion relative to the proximal portion causes the actuator to engage the detent and provide a signal.

8. The fixation tool of claim 7, further comprising a handle depending from the distal portion.

9. The fixation tool of claim 7, further comprising a gripping surface disposed on the proximal portion.

10. The fixation tool of clam 7, wherein the proximal portion is rotatably coupled with the distal portion.

11. The fixation tool of claim 10, wherein the engagement collar is coupled with the proximal portion.

12. The lead fixation tool of claim 7, wherein the signal is audible.

13. The lead fixation tool of claim 7, here the signal is a tactile sensation.

14. A lead fixation tool comprising:
a housing having a generally circular cross section, the housing including a proximal portion and a distal portion, wherein the proximal portion and the distal portion are axially aligned, wherein the proximal portion and the distal portion are rotatably coupled;
a guide passage for receiving stylet and extending between an opening in the proximal portion to a lumen interface, wherein the guide passage tapers from a larger diameter at the opening to a narrower diameter distal from the opening;
a lead receiving channel disposed within the distal end for receiving at least a portion of a connector assembly of a lead, the lead receiving channel having a longitudinal axis;
an expandable connector pin channel disposed within the lead receiving channel for receiving a connector pin of the connector assembly and axially aligning the connector pin with the lumen interface; and
an engagement collar defining the connector pin channel and configured to grip the connector pin, wherein the engagement collar is a C-shaped interference clamp that is axially aligned with the lead receiving channel to grip a lead connector assembly and remain at a fixed location on said longitudinal axis during said relative rotation of said proximal and distal portions with the proximal; and
a rotation indicator for indicating relative rotation between the proximal and distal portions while the lead connector assembly is engaged by the C-shaped interference clamp wherein the rotation indicator includes:
a resilient arm having an actuator: and
a detent, wherein rotation of the distal portion relative to the proximal portion causes the actuator to engage the detent and provide a signal.

15. The lead fixation tool of claim 14, further comprising a handle depending from the distal portion in a plane that is perpendicular to an axis of rotation of the tool.

16. The lead fixation tool of claim 14, further comprising a gripping surface disposed over at least a portion of an exterior of the proximal portion.

17. The lead fixation tool of claim 16, wherein the gripping surface includes a plurality of ridges.

18. The lead fixation tool of claim 14, further comprising a directional indicator for indicating a direction of rotation to affect lead implantation.

19. The lead fixation tool of claim 14, wherein the proximal portion is rotatable relative to the distal portion.

20. The lead fixation tool of claim 19, further comprising a bearing forming an interconnection between the proximal portion and the distal portion.

21. The lead fixation tool of claim 14, wherein the resilient arm is coupled with the proximal portion and the detent is formed in the distal portion.

22. The lead fixation tool of claim 21, further comprising a window disposed on the distal portion that permits visual observance of the actuator engaging the detent.

23. The lead fixation tool of claim 14, wherein the signal is audible.

24. The lead fixation tool of claim 14, wherein the signal is a tactile sensation.

25. The lead fixation tool of claim 14, wherein the guide passage is configured to receive a portion of a handle of the stylet.

26. The lead fixation tool of claim 14, wherein the housing is aligned parallel to the connector pin during rotation of the tool.

* * * * *